(12) United States Patent
Kwok et al.

(10) Patent No.: US 10,758,690 B2
(45) Date of Patent: Sep. 1, 2020

(54) METHODS AND APPARATUS FOR IMPROVING CPAP PATIENT COMPLIANCE

(71) Applicant: ResMed Pty Ltd, Bella Vista, New South Wales (AU)

(72) Inventors: Philip Rodney Kwok, Sydney (AU);
Ron Richard, Escondido, CA (US);
Rohan Mullins, Sydney (AU); Chee Keong Phuah, Sydney (AU);
Karthikeyan Selvarajan, Sydney (AU); Adrian Barnes, Sydney (AU);
Christopher Kingsley Blunsden, Sydney (AU); Benriah Goeldi, Freiburg (DE)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 14/968,243

(22) Filed: Dec. 14, 2015

(65) Prior Publication Data
US 2019/0224431 A1  Jul. 25, 2019

Related U.S. Application Data

(63) Continuation of application No. 11/921,757, filed as application No. PCT/AU2006/000824 on Jun. 14, 2006, now Pat. No. 9,227,032.

(30) Foreign Application Priority Data

| Jun. 14, 2005 | (AU) | 2005903089 |
| Nov. 4, 2005 | (AU) | 2005906122 |
| Nov. 8, 2005 | (AU) | 2005906193 |

(51) Int. Cl.
*A61M 16/00* (2006.01)
*A61M 16/06* (2006.01)

(52) U.S. Cl.
CPC .... *A61M 16/0051* (2013.01); *A61M 16/0069* (2014.02); *A61M 16/024* (2017.08);
(Continued)

(58) Field of Classification Search
CPC ............ A61M 16/024; A61M 16/0051; A61M 16/0069
See application file for complete search history.

(56) References Cited

U.S. PATENT DOCUMENTS

| 4,944,310 A | 7/1990 | Sullivan |
| 5,199,424 A | 4/1993 | Sullivan et al. |

(Continued)

FOREIGN PATENT DOCUMENTS

| DE | 19750536 | 5/1999 |
| DE | 102 53 934 | 12/2003 |

(Continued)

OTHER PUBLICATIONS

European Search Report issued in EP Patent Application No. EP 06741236 dated Oct. 18, 2011.

(Continued)

*Primary Examiner* — LaToya M Louis
(74) *Attorney, Agent, or Firm* — Nixon & Vanderhye P.C.

(57) ABSTRACT

A method of operating a device for treating sleep disordered breathing (SDB), wherein the device provides continuous positive airway pressure during sleep, includes applying a treatment pressure to a patient, monitoring the patient for speech output, generating a signal in response to detected speech of the patient, and, in response to the signal, reducing the treatment pressure applied to the patient.

16 Claims, 7 Drawing Sheets

(52) U.S. Cl.
CPC ..... *A61M 16/06* (2013.01); *A61M 2016/0021* (2013.01); *A61M 2016/0027* (2013.01); *A61M 2016/0036* (2013.01); *A61M 2205/15* (2013.01); *A61M 2205/502* (2013.01); *A61M 2205/52* (2013.01); *A61M 2205/80* (2013.01)

(56) References Cited

U.S. PATENT DOCUMENTS

| | | | |
|---|---|---|---|
| 5,245,995 | A | 9/1993 | Sullivan et al. |
| 5,522,382 | A | 6/1996 | Sullivan et al. |
| 5,704,345 | A | 1/1998 | Berthon-Jones |
| 6,029,665 | A | 2/2000 | Berthon-Jones |
| 6,112,746 | A | 9/2000 | Kwok et al. |
| 6,138,675 | A | 10/2000 | Berthon-Jones |
| 6,305,372 | B1 | 10/2001 | Servidio |
| 6,357,441 | B1 | 3/2002 | Kwok et al. |
| 6,363,933 | B1 | 4/2002 | Berthon-Jones |
| 6,398,739 | B1 | 6/2002 | Sullivan et al. |
| 6,581,602 | B2 | 6/2003 | Kwok et al. |
| 6,634,358 | B2 | 10/2003 | Kwok et al. |
| 6,635,021 | B1 | 10/2003 | Sullivan et al. |
| 6,997,178 | B1* | 2/2006 | Reynaud ............... A62B 18/08 128/201.19 |
| 2002/0166557 | A1* | 11/2002 | Cooper ................ H04R 1/083 128/206.28 |
| 2003/0221687 | A1 | 12/2003 | Kaigler |
| 2005/0011520 | A1* | 1/2005 | Rowe .................... A62B 25/00 128/205.22 |
| 2005/0066970 | A1 | 3/2005 | Donofrio |
| 2005/0126571 | A1* | 6/2005 | Jorczak ............ A61M 16/0672 128/205.24 |
| 2005/0235993 | A1 | 10/2005 | Baecke et al. |
| 2009/0205662 | A1 | 8/2009 | Kwok et al. |
| 2010/0263664 | A1* | 10/2010 | Radivojevic ...... A61M 16/0666 128/202.26 |

FOREIGN PATENT DOCUMENTS

| | | |
|---|---|---|
| EP | 1 120 124 | 8/2001 |
| JP | H06-509487 | 10/1994 |
| JP | 07-265430 | 10/1995 |
| JP | 2001-505085 | 4/2001 |
| JP | 2001-245984 | 9/2001 |
| JP | 2002-165885 | 6/2002 |
| JP | 2003-521272 | 7/2003 |
| JP | 2004-535226 | 11/2004 |
| WO | 92/22244 | 12/1992 |
| WO | 98/14116 | 4/1998 |
| WO | 2001/32069 | 5/2001 |
| WO | 2001/97893 | 12/2001 |
| WO | 02/096342 | 12/2002 |
| WO | 2003-527160 | 9/2003 |
| WO | 2004/045692 | 6/2004 |
| WO | 2005/051470 | 6/2005 |

OTHER PUBLICATIONS

Office Action issued in Japanese Application No. 2008-516072 dated Jul. 5, 2011 with English Translation.
International Preliminary Report on Patentability for PCT/AU2006/000824, dated Dec. 17, 2007.
PCT International Search Report dated Jul. 10, 2006.

* cited by examiner

METHODS AND APPARATUS FOR IMPROVING CPAP PATIENT COMPLIANCE

CROSS REFERENCE TO RELATED APPLICATIONS

This application is the continuation of U.S. application Ser. No. 11/921,757, filed Dec. 7, 2007, which is the U.S. National Phase of International Application No. PCT/AU2006/000824, filed Jun. 14, 2006 which designated the U.S. and claims the benefit of Australian Application No. AU2005903089, filed Jun. 14, 2005, Australian Application No. AU2005906122, filed Nov. 4, 2005, and Australian Application No. AU2005906193, filed Nov. 8, 2005, each of which is incorporated herein by reference in its entirety.

BACKGROUND OF THE INVENTION

1. Field of the Invention

This invention relates to mechanical ventilation of sleep disordered breathing (SDB), and in particular to methods and apparatus for improving patient compliance in Continuous Positive Airway Pressure (CPAP) treatment.

2. Description of Related Art

A comprehensive background discussion of mechanical ventilation can be found in "Principles and Practice of Mechanical Ventilation" (1994) edited by Martin J Tobin, published by McGraw-Hill Inc., ISBN 0-07-064943-7.

The use of nasal Continuous Positive Airway Pressure (CPAP) to treat Obstructive Sleep Apnea (OSA) was invented by Colin Sullivan, see U.S. Pat. No. 4,944,310. Generally, the treatment involves providing a supply of air or breathable gas from a blower to a patient via an air delivery conduit and a patient interface, such as a full-face or nasal mask, or nasal prongs. While treatment is effective, some patients find it uncomfortable. Improving patient comfort and compliance is a continuing challenge.

One way to improve comfort is to provide a more comfortable patient interface. In this regard, the ResMed MIRAGE™ masks have provided significant improvement in comfort. See U.S. Pat. Nos. 6,112,746; 6,357,441; 6,581, 602; and 6,634,358. A more recent development is the ResMed MIRAGE™ ACTIVA™ mask series. See International Patent Application WO 2001/97893.

In the early days of nasal CPAP systems for treating OSA, patients were first titrated in a clinical study to determine an optimal treatment pressure. Titration involves a patient sleeping overnight in a clinic and being tested with a mask and CPAP device. The treatment pressure provided by the CPAP device is adjusted until apneas are eliminated. The treatment pressure is usually in the range of 4-20 cmH$_2$O. A device would be set to that pressure and given to the patient to take home. A subsequent development was the automatically adjusting device that a patient could take home. The automatically adjusting device will raise and/or lower the treatment pressure based on indications of obstructive sleep apnea, such as snoring. Such CPAP devices are sometime generically referred to as Automatic Positive Airway Pressure (APAP) devices. See U.S. Pat. Nos. 5,245,995; 6,398,739; and 6,635,021.

Another type of nasal CPAP device provides a first pressure during inhalation (sometimes termed an IPAP) and a second, lower pressure during exhalation (sometimes termed an EPAP). Examples of these include the ResMed VPAP™ series, and the Respironics BiPAP series. Bilevel CPAP devices may be prescribed for patients who do not comply with single pressure CPAP devices. Some patients perceive that the lower pressure during exhalation is more comfortable, at least while they are awake.

Another way of improving patient comfort and compliance is to start each therapy session at a low therapeutic pressure, e.g., 4cmH$_2$O, and ramp up to full therapeutic pressure over the first hour, to allow the patient to adjust to the sensation while falling asleep. Alternatively, the device may set to implement a time delay before full therapeutic pressure is applied, to allow the patient time to fall asleep before full therapeutic pressure is applied. See U.S. Pat. Nos. 5,199,424 and 5,522,382.

Another form of automatically adjusting CPAP device is the ResMed AUTOSET™ SPIRIT™ device. In this device, the CPAP pressure is automatically increased or decreased in accordance with indications of flow limitation, such as flow flattening, snore, apnea and hypopnea. See U.S. Pat. Nos. 5,704,345; 6,029,665; 6,138,675; and 6,363,933. An advantage of an automatically adjusting system is that over time the treatment pressure required may vary for a particular patient and a correctly functioning automatic system can obviate the need for the patient to return for a subsequent sleep study. These patents also describe a method and apparatus for distinguishing between so-called "central" and obstructive apneas.

The contents of all of the aforesaid patents are incorporated by cross-reference.

Some OSA patients find treatment with the above devices uncomfortable and they become non-compliant with the therapy. Other patients such as cardiovascular patients with Congestive Heart Failure, patients with REM Hypoventilation, and patients with Respiratory Insufficiency could also benefit from a more comfortable and/or effective form of therapy.

One hurdle in patient compliance occurs in the initial stages of treatment, where a patient may have difficulty in adjusting to the sensations of the therapy and may quit therapy before realizing the benefits of the therapy.

A further hurdle to patient acceptance of the therapy is in the initial fitting of the patient interface (e.g., mask), where the mask fit is tested under relatively low pressure and high flow. This may result in noisy operation of the device and high flow air leaks as the mask is adjusted to the patient, which can be a noisy and unsettling initial experience for the patient.

Other impediments to patient comfort and compliance include the treatment impeding the ability of the patient to communicate to the clinician or bed partner, or the patient or bed partner being disturbed by air leaks from the mask.

SUMMARY OF THE INVENTION

One aspect of the invention relates to a method and apparatus to overcome or ameliorate one or more of these disadvantages.

'Easy Speak'

A first aspect of the invention relates to a method of operating a device for treating sleep disordered breathing (SDB), wherein said device provides continuous positive airway pressure during sleep, the method comprising:

applying a treatment pressure to a patient;

monitoring the patient for speech output;

generating a signal in response to detected speech of the patient; and in response to said signal, reducing the treatment pressure applied to the patient.

In an embodiment, in response to the signal the treatment pressure is reduced for a predetermined period of time.

In one embodiment, the monitoring the patient includes sensing sounds made by the patient and analyzing the sounds to detect speech. The analysis may include filtering of the sounds to remove non-speech sound.

In another embodiment, the monitoring the patient includes detecting expiration patterns indicative of speech. The monitoring of the patient may include detecting pressure and/or flow signals by the device, filtering these signals to remove those indicative of snoring and analyzing the filtered signals.

In another form, the monitoring of the patient includes sensing of sounds made by the patient and detection of the arousal state of the patient. For example, patient sounds made while the patient is awake may be identified as speech.

In a further form, the monitoring of the patient includes monitoring sounds made by the patient within a predetermined time from the start of a therapy session. The function may be disabled after the predetermined time from the start of the session.

In one form, the speech includes humming.

Alternatively, monitoring the patient may include detecting vibration indicative of speech, for example by detecting the vocal cord vibration on the patient's neck.

A further aspect of the invention relates to a method of operating a device for treating sleep disordered breathing (SDB), wherein said device provides continuous positive airway pressure during sleep, the method comprising:
applying a treatment pressure to a patient;
monitoring the patient for speech output;
generating a signal in response to detected speech of the patient; and
in response to said signal, controlling one or more functions of the device.

In this form, monitoring the patient includes checking the speech against one or more vocal commands programmed into the device, recognizing a match between the speech and a vocal command and controlling a function of the device associated with the vocal command.

In one form, monitoring the patient compensates for changes in speech characteristics due to application of treatment pressure, optionally by detecting speech characteristics which are less affected by the application of treatment pressure.

Another aspect of the invention relates to a method of operating a device for treating sleep disordered breathing (SDB), wherein said device provides continuous positive airway pressure during sleep, the method comprising:
applying a treatment pressure to a patient;
monitoring the patient for speech output;
generating a signal in response to detected speech of the patient; and
in response to said signal, reducing the treatment pressure applied to the patient for a predetermined period of time.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Hardware

A positive airway pressure (PAP) device in accordance with an embodiment of the invention includes a blower and blower-controller. The blower can deliver a supply of air at positive pressure 2-40 cmH$_2$O, but generally in the range of 4-20 cmH$_2$O to a patient interface via an air delivery conduit.

The device also includes a flow sensor to measure the flow of air along the conduit, and pressure sensors to measure the pressure of air at the blower outlet.

In one form, the device alternatively includes an additional pressure sensor to detect the pressure in the patient interface.

Figure 1:
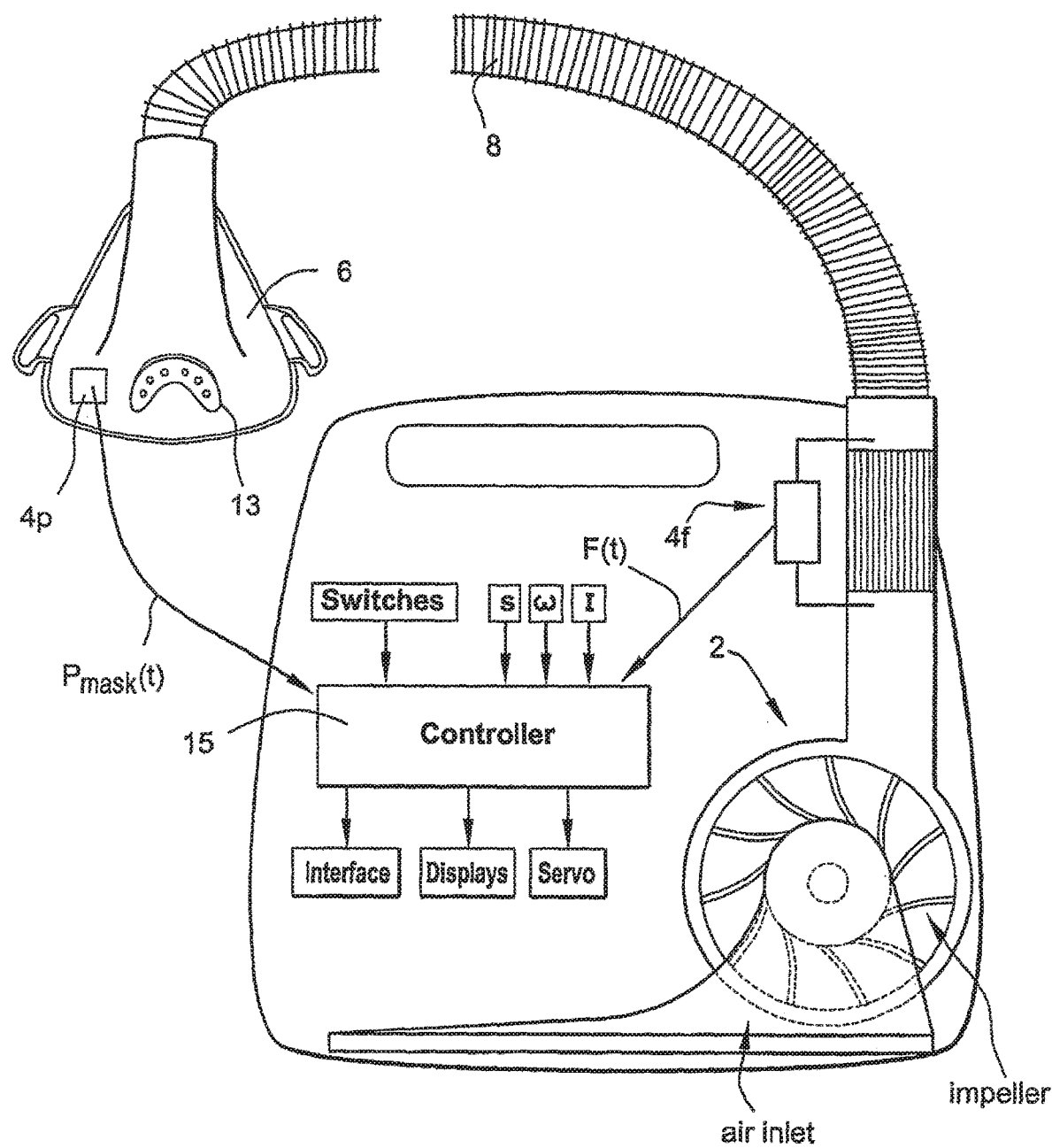
FIG. 1 illustrates a ventilator apparatus according to an embodiment of the present invention for implementing methods according to embodiments of the invention.

For example, FIG. 1 illustrates a ventilator device according to an embodiment of the invention. As illustrated, the ventilator device may include a servo-controlled blower 2, a flow sensor 4$f$, pressure sensor 4$p$, a mask 6, and an air delivery conduit 8 for connection between the blower 2 and the mask 6. Exhaust gas is vented via exhaust 13.

Mask flow may be measured by a flow sensor, such as a pneumotachograph and differential pressure transducer to derive a flow signal F(t). Alternatively, the pneumotachograph may be replaced by a bundle of small tubes aligned in parallel with the flow from the blower with the pressure difference measured by the differential pressure transducer across the bundle.

Mask pressure is preferably measured at a pressure tap using a pressure transducer to derive a pressure signal P$_{mask}$(t). The pressure sensor 4$p$ and flow sensor 4$f$ have been shown only symbolically in FIG. 1 since it is understood that those skilled in the art would understand how to measure flow and pressure.

Flow F(t) and pressure P$_{mask}$(t) signals are sent to a controller or microprocessor—referred to herein as processor 15—to derive a pressure request signal P$_{Request}$(t). The controller or processor is configured and adapted to perform the methodology described in more detail herein. The controller or processor may include integrated chips, a memory and/or other instruction or data storage medium to implement the control methodology. For example, programmed instructions with the control methodology are either coded on integrated chips in the memory of the device or loaded as software. As those skilled in the art will recognize, analogue devices may also be implemented in the control apparatus.

The controller or processor 15 is further adapted to derive parameters indicative of the patient's breathing and sleep pattern, such as for deriving indications of flow limitation, such as flow flattening, snore, apnea and hypopnea and the Apnea Hypopnea Index (AHI), and for distinguishing between REM and non-REM sleep. See U.S. Pat. Nos. 5,704,345 and 6,029,665.

The apparatus of FIG. 1 includes other sensors, communication interfaces and displays, a servo, etc., and functional blocks the details of which are not necessary for an understanding of the present invention.

Acclimatization Therapy for First Time Users

Figure 2:
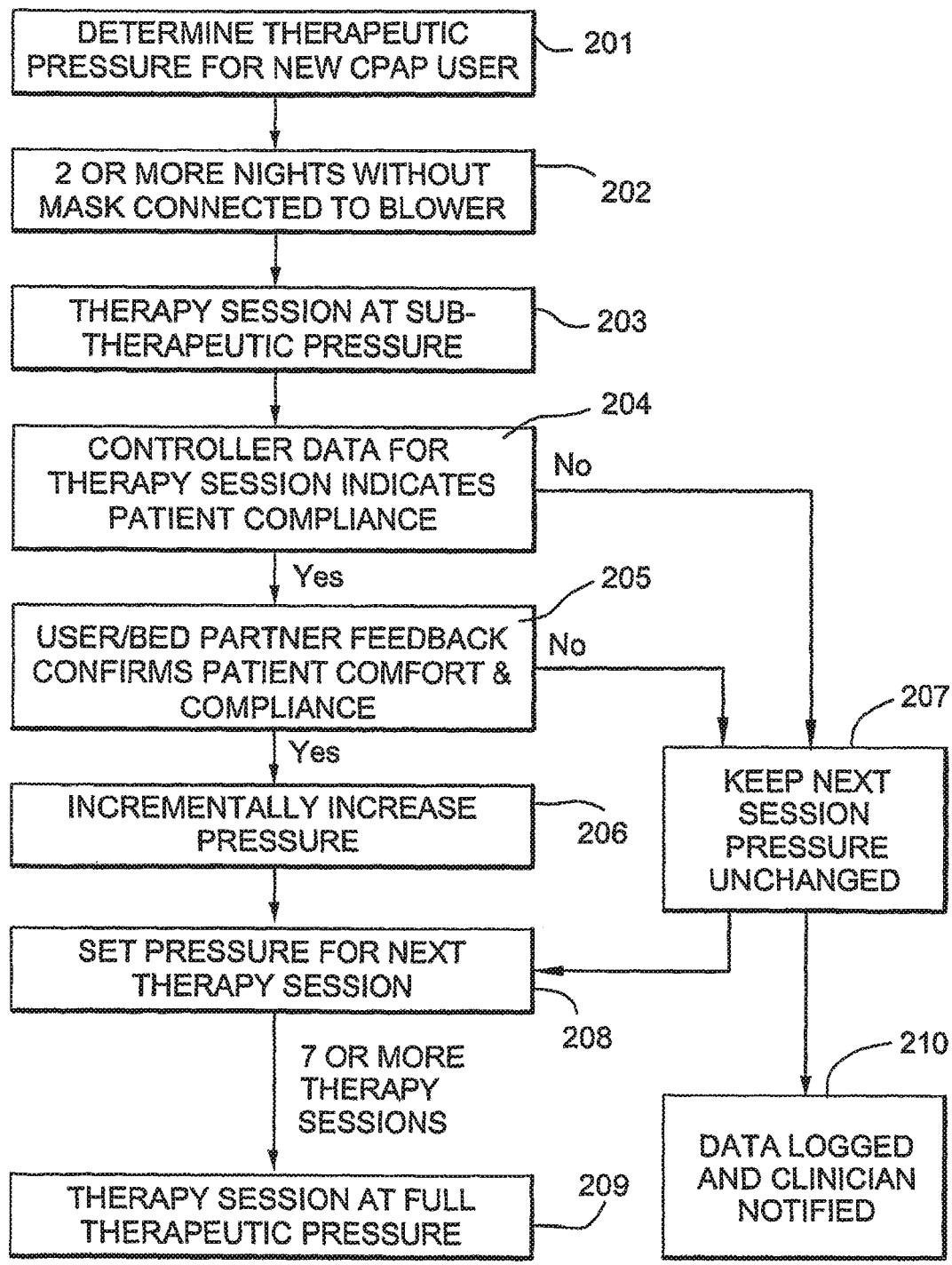
FIG. 2 is a flowchart illustrating an acclimatization therapy for new users of CPAP treatment according to an embodiment of the invention.

FIG. 2 illustrates an acclimatization therapy for new users of CPAP therapy according to an embodiment of the invention.

After initial set up by a clinician, including setting of a full therapeutic pressure (step 201), the patient is sent home with a CPAP mask and blower.

For the first few nights of the acclimatization therapy (e.g., two or more nights), the patient is provided with a headgear and mask from which the elbow and gas conduit have been disconnected, thus allowing the patient to first become accustomed to the feel of the mask and headgear during sleep, without additional impediments such as the noise and air pressure generated by the blower (step 202).

For the next step in the acclimatization therapy, the elbow and gas conduit are connected to the mask, and the blower is turned on.

The blower is set to a "first timer mode" (also referred to herein as a "Max Ramp" or "AccliMATE" mode), in which the treatment pressure for the entire first CPAP session is provided at a sub-therapeutic pressure, for example at 2 cmH$_2$O (step 203).

Before the start of the second CPAP session, a series of preprogrammed patient and/or bed partner feedback questions are displayed on the machine display, the responses to which are used in setting the treatment pressure for the next session. For example, the patient may be asked to provide a yes/no answer, or a rating out of ten, to questions relating to treatment comfort, and the patient and/or the bed partner may be asked to respond to questions relating to patient restlessness and sleep quality.

If the patient and/or bed partner responses are sufficiently favorable to indicate that the patient is adjusting to the sensations of the therapy, and the recorded measurements of the treatment session indicate substantial patient compliance with the therapy (steps 204 and 205), the pressure for the next session is incrementally increased (step 206), e.g., by 1 cmH$_2$O. If the responses do not indicate patient acclimatization, or if other indicators of patient compliance for the session are negative (for example indicating that the patient removed the mask for a substantial period) (steps 204 and 205), the treatment pressure is not increased (step 207), e.g., pressure unchanged.

The pressure is set for the next therapy session (step 208), and the process of patient feedback and incremental increase in treatment pressure is repeated until full therapeutic pressure is reached, e.g., after 7 or more sessions (step 209). In the case of APAP treatment, once the treatment pressure reaches a therapeutic pressure of 4 cmH$_2$O, the treatment pressure may be a capped maximum pressure for the session. In the case of bilevel CPAP treatment, either just the inhalation (IPAP) pressure may be capped or both the IPAP and the exhalation (EPAP) pressure may be scaled down correspondingly.

If more than a predetermined number of successive—or cumulative—negative feedback responses are recorded, the controller will cause display of a message advising the patient to contact the clinician. If the device is connected to external communication, e.g., to the telephone network, the notification may be sent directly to the clinician, e.g., data logged and clinician notified (step 210).

Details of the patient feedback responses, and the treatment pressures may be stored in the controller for later review by the clinician.

In an embodiment, the controller may be programmable by the clinician using the menu system to alter the parameters of the 'first timer' mode, for example, to set the initial therapy session pressure and/or the daily pressure increment according to the severity of the patient's sleep disordered breathing and the clinician's opinion of how long the patient may take to acclimatize to the sensations of the CPAP therapy.

The acclimatization therapy thus allows the patient to gradually adjust to the sensations of CPAP therapy, with the progression profile of the acclimatization controlled according to patient feedback. It is expected that adoption of this approach will increase the chance of patient compliance during the early stages of therapy, and therefore increase long-term acceptance and compliance.

Figure 2A:
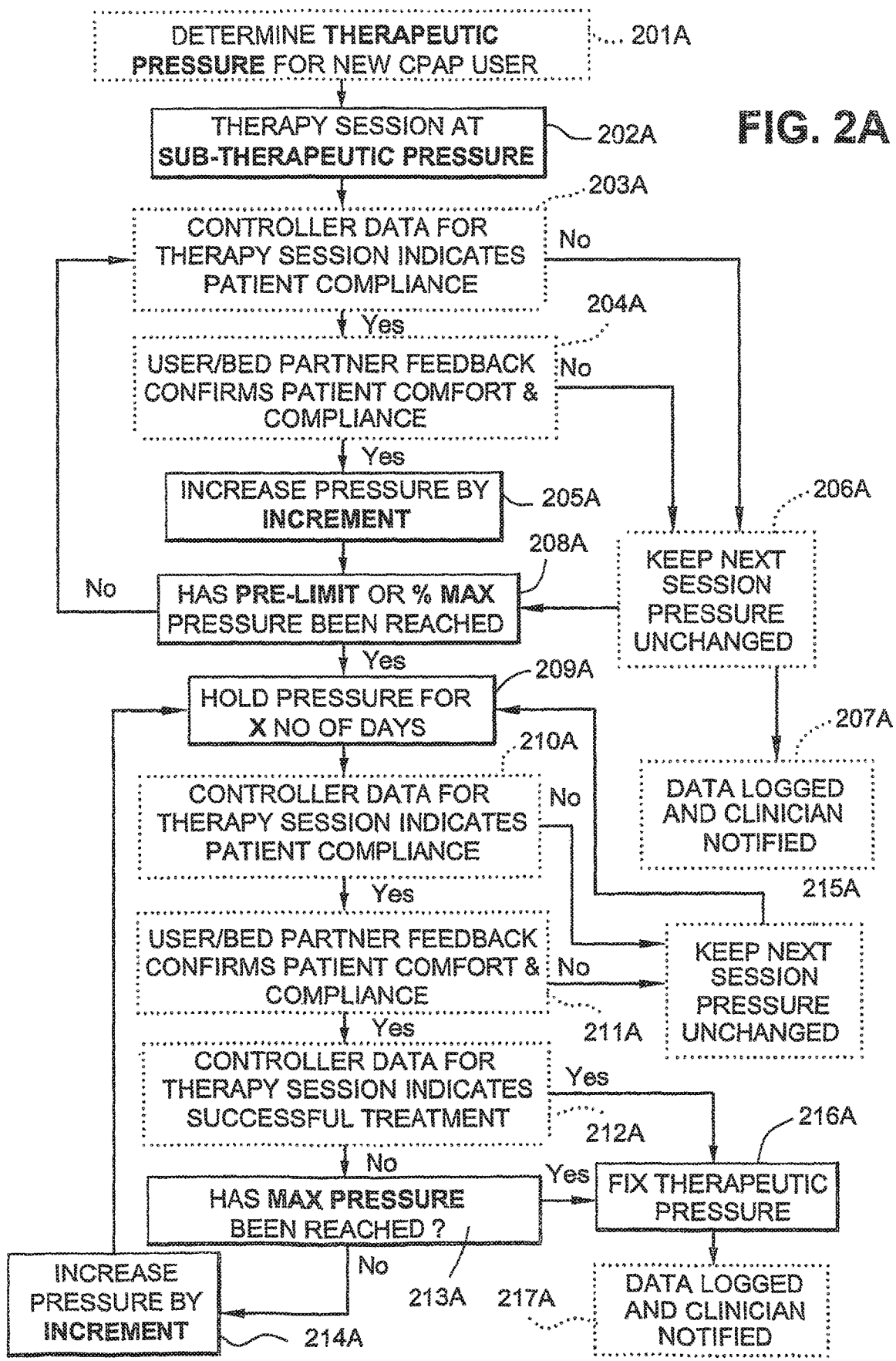
FIG. 2A is a flowchart of an acclimatization therapy for new CPAP users according to another embodiment of the invention.

FIG. 2A illustrates a modified form of acclimatization therapy for first time CPAP users, which is adapted to help in setting of an appropriate maximum treatment pressure.

In the embodiment of FIG. 2A, the clinically-derived full therapeutic pressure for the patient is determined by the clinician in a titration study (step 201A).

In the acclimatization therapy, the CPAP device includes a 'Max Ramp' feature which is programmed to hold a maximum pressure for a preprogrammed day number (step 209A) and monitor the patient's respiratory events via the device's monitoring capabilities, such as the ResTraxx™ function of ResMed machines to see if that pressure is the correct one. Steps 202A-207A are similar to steps 203-207, and 210 of FIG. 2 described above. The maximum pressure is incrementally increased each day until a preset percentage or pressure differential from the titrated maximum pressure is reached (step 208A), and is held there (step 215A) or increased (step 214A) based on monitored treatment effectiveness, the presence/absence of respiratory events, clinician review, or may be based upon user/bed partner feedback, comfort and compliance (steps 210A, 211A, 212A) such as that illustrated in FIG. 2. Once maximum pressure is reached (step 213A) and/or therapy session indicates successful treatment (step 212A), the therapeutic pressure is fixed (step 216A) and data logged and clinician notified (step 217A).

For example, a new CPAP patient may be titrated in a sleep study and a maximum treatment pressure of 12 cmH$_2$O may be prescribed. On the first night of treatment the treatment ramps from 4 to 5 cm over the first 45 minutes of treatment. On the next night the pressure ramps up over 45 minutes from 5 cm to 6 cm and so on until it gets to within a predetermined amount—for example 4 cmH$_2$O—or a predetermined percentage—such as 80%—of the prescribed maximum treatment pressure. So in this example the CPAP machine may be programmed by the clinician to stop the daily increase at a pressure of 8 (i.e., 12−4) cmH$_2$O for a set number of days (e.g., up to 7 days) to monitor the patient airway using the monitoring functions of the CPAP machine. If the patient is not having adverse respiratory events at say the pressure of 10 cm, then the maximum treatment pressure may be fixed at that level rather than progressing to the originally-prescribed level of 12. If the patient is still having adverse respiratory events at a pressure of 12, then the machine may increase it or refer the patient to the clinician for a decision on whether to increase the treatment pressure.

It is envisaged that this acclimatization therapy would give at least some of the benefits of the AutoSetting function of an AutoSet CPAP machine but resulting in a fixed pressure that many Doctors/Clinicians are comfortable with rather than AutoSetting adjustment of the treatment pressure breath-by-breath. This keeps greater control of the set pressure in the hands of the clinician, which some patients and clinicians may be more comfortable with. This acclimatization may also be used as a stepping stone to getting patients and clinicians accustomed to AutoSetting functions.

In the flowchart of FIG. 2A, those items in bold may be preset or prescribed by the clinician (e.g., initial sub-therapeutic pressure, increment pressure, max pressure, pre-limit or % of max pressure, X no. of days to hold at pre-limit or % of max pressure, no. of events or other criteria that indicates successful treatment). Those boxes in dashed lines may optionally be omitted.

Possible advantages of the acclimatization therapy of FIG. 2A include improvement in the treatment of patients where the prescribed pressure is too high or too low, with consequent reduction in therapist's time treating those patients. Such patients currently take a substantial amount of therapist's time for treatment because they are being over treated or under treated and furthermore these patients are often not happy/compliant. The stair stepping approach of the 'Max Ramp' feature could cut the costs of treatment of such patient by helping to determining the appropriate pressure with minimal therapist intervention. The method may be carried out with modifications based on a ResMed Elite machine or a ResMed ResTraxx machine, both of which are less expensive machines than one having full AutoSet capabilities. If the prescribed pressure was determined to be wrong, the home medical equipment (HME) provider could send the patient a card to change the pressure; simple and cost effective. Also, the method includes minimal work from the patient, which helps to achieve new patient compliance and acceptance of the treatment.

A further embodiment of the invention provides a simplified acclimatization therapy ("Max ramp") mode with greater control by the clinician.

In this embodiment, the machine is programmable to increase the maximum treatment pressure automatically over time. The Clinician could program the start pressure, say 4 cm, and have the device ramp up to the prescribed pressure over a set period of time with no patient involvement.

For example, start pressure may be set at 4 cm and maximum pressure set at 10. The clinician could prescribe a Max Ramp of 6 days. On Day 1 the device would start at 4 cm and stay at 4 cm all night. On day 2 the device would start at 4 and ramp, depending on the set ramp time (max 1 hour), to 5 cm and stop. Day 3 start at 4 cm and ramp to 6 cm, and so on until the set maximum therapeutic pressure is reached.

The clinician would choose the number of days the Max ramp was to occur and the device would calculate the daily increase in a linear or other predetermined fashion. Alternatively the clinician could set the start pressure and start Max Ramp feature. For example, start pressure 4 cm and stop at the start Max Ramp Feature of 7 cm, max pressure=12 cm. In this scenario, day one the device would start at 4 cm, ramp to 7 cm over the ramp time (max 1 hour) then hold there for the first night. On day 2 the device would start at 4 cm, ramp (max 1 hour) to 8 cm (or what ever the linear calculation says, and stop) and so on throughout the set time for the Max Ramp.

Optionally, the clinician could choose a machine mode which allows the patient to hold at a pressure for an additional night if the patient feels the pressure is becoming too much. This could be accomplished by pressing a sequence of buttons on the device. This machine mode also allows programming by the clinician to set boundary conditions on the acclimatization therapy ("Max ramp") mode.

For example, the machine display may prompt the patient at the end of each daily session to enter a response indicating how they coped with the therapy. The patient could press "Okay" or "Not okay". If many subsequent days are "okay", the machine increases the daily ramp increment to ramp to prescribed maximum therapy pressure more aggressively, thus bringing the patient to therapy as early as possible. If the patient responses indicate that the patient is struggling to acclimatize to therapy (e.g. two consecutive days of "Not Okay"), the daily ramp increment is decreased to extend the acclimatization period, within the clinician-set boundaries.

More than a preset number of daily "Not okays" may cause the device to prompt the patient with help details (visual and/or audible methods) and/or request patient to contact clinician before getting too frustrated with the therapy, thus potentially reducing drop-outs even further. Where the device has communication capabilities, the device may also contact the clinician directly to get into contact with the patient.

Further details of the process phases, the machine modes and an example of this embodiment are set out below.

A. Acclimatization Process Phases:
The acclimatization therapy goes through three phases:
1. Initiation Phase: Physician or Clinician prescribes an "AccliMATE" mode
2. AccliMATE Phase: the AccliMATE mode automatically adjusts nightly CPAP pressure until final set-point CPAP pressure is reached according to physician or clinician
3. Standard CPAP Phase: Flow Generator Operates in Standard CPAP mode B. AccliMATE Mode Detail:
1. Physician/Clinician Adjustable Parameters:
   (a) Adjustment period (settable range): 1-30 days
   (b) End target CPAP setting ("T"): 4-20 cm $H_2O$
   (c) Starting night #1 CPAP setting ("S"): 4-*$H_2O$ (can only be set where "S"<"T")
   (d) Optional patient "snooze" button function. When pressed by the patient this would maintain previous day's CPAP pressure setting for a physician/clinical set limited number of days at any individual pressure. Settable range=0-5 days. This snooze function can be turned off or can allow the patient to remain at any one pressure for a limited number of days if they push the "snooze' button at the beginning of the next night's session during the CPAP AccliMATE phase.

Note: standard nightly ramp from 4 cm $H_2O$ to that night's set point can be set as normal from 0-45 minutes using standard ramp function 2. Machine calculation modes:
   (a) Linear
   (b) Logarithmic
   (c) Exponential
   (d) Step-function (0.5 cm/day, 1 cm/day, 2 cm/day, 3 cm/day, etc.)
   (e) Other formulae C. Example:
Clinician/Physician sets:
   (a) Adjustment period=7 days
   (b) End target CPAP=10 cm H2O
   (c) Starting CPAP=4 cm H2O
   (d) Patient Snooze=0 days (i.e., off)

| Day # | 1 | 2 | 3 | 4 | 5 | 6 | 7 |
|---|---|---|---|---|---|---|---|
| CPAP | 4 cmH$_2$O | 5 cmH$_2$O | 6 cmH$_2$O | 7 cmH$_2$O | 8 cmH$_2$O | 9 cmH$_2$O | 10 cmH$_2$O |

Easy Speak

Figure 3:
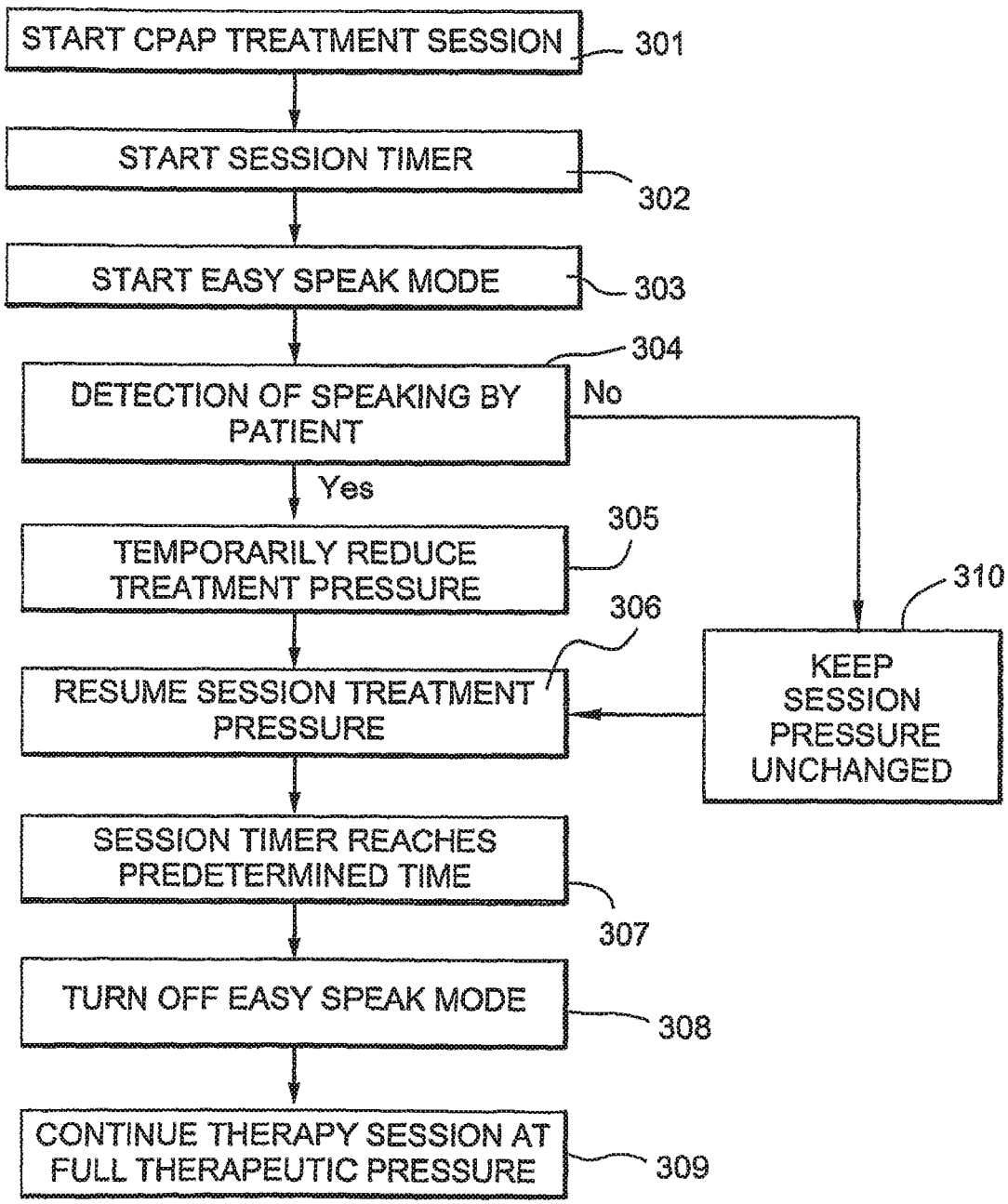
FIG. 3 is a flowchart illustrating a method of control of the CPAP therapy to facilitate speech by the patient during treatment according to an embodiment of the invention.

A further embodiment of the invention, illustrated in FIG. 3, facilitates verbal communication by the patient to a clinician or bed partner during treatment.

At the commencement of the therapy session (step 301), the session timer of the controller is started (step 302), and the 'easy speak' mode of the blower is activated step (step 303).

In this mode, the controller is adapted to determine speech by the patient (step 304). Such detection may be, for example, by means of a microphone (not shown) at the patient interface, connected back to the controller, with filtering or signal processing means adapted to distinguish between frequencies and patterns indicative of the sounds of speech rather than of snoring, or by detection of expiration patterns or other breathing patterns typical of speech. By combining the pressure/microphone signal (or some signal derived from it) and the flow or rate of change of flow, more accurate speech detection may be possible.

One means of implementing the determination of speech is to employ voice recognition technology, which is in itself well known in other fields such as in hands-free typing software and mobile telephones. Voice recognition technology allows a distinction to be made between speech by a particular person and other sounds and other people speaking within the same environment. Other developments in distinguishing between types of sounds include the technology employed in noise-canceling headphones, such as those developed by Bose Corporation of USA.

The device may be programmed to recognize certain vocal commands spoken by the patient, and upon matching the vocal commands to its programmed vocabulary of words will implement an associated control function of the device. For example, the machine may be 'trained' to recognize the patient speaking the words "stop" to stop the flow generator, "start" to restart, and "talk" to implement the speech mode as described below. In this way, the machine may be controlled.

Upon detection of speech by the patient, the pressure provided by the blower is temporarily reduced or stopped for a first predetermined time (step 305), for example of 5-60 seconds, or more preferably during the entire period of detected speech, thus allowing the patient to speak without the resisting pressure. If within this time the patient ceases to speak for a second predetermined period (for example, 2 to 5 seconds), the treatment pressure may be resumed, or gradually increased (step 306). In Autoset® devices, the pressure may be resumed at the minimum pressure. Also, the treatment pressure resumes unchanged if speech is not detected by easy speak mode (step 310).

By reducing the treatment pressure when the patient is attempting to speak, the sensation—which some patients find discomforting—of air rushing out as the patient speaks is minimized, and communication with the patient's bed partner and/or family or with the clinician becomes easier. It is believed that this will make the therapy easier to adjust to and reduce another impediment to patient compliance with the therapy.

To reduce the possibility of false positive detection of speech, and the undue interruption of therapy that this may cause, the controller is programmed to turn off the easy speak mode (step 308) once a certain time of the therapy session has elapsed (step 307). If desired, this time period may be selectable by the patient via the set up menu of the blower, within certain limits. For example, the patient may be able to input a time of 15 to 60 minutes, depending on how long it will typically take that patient to fall asleep. The set up menu of the machine may also allow the patient turn off the easy speak mode altogether. After easy speak mode is turned off, the therapy session continues at full therapeutic pressure (step 309).

Where the flow generator is of the type in which the treatment pressure is ramped up over a 5 to 20 minute period at the beginning of each treatment session, the 'easy speak' mode may be activated only during that initial period in which the pressure is being increased, and disabled once the flow generator reaches full therapeutic pressure.

The easy speak mode may also be activated when the device is set to a fitting mode, so that patient communication to the clinician is improved when the mask is being fitted.

Instead of, or in addition to, the illustrated embodiment in which the controller uses the session timer to control whether the easy speak mode is activated, it is possible to use other indicators of the patient's sleep state to activate the easy speak when the patient is awake.

For example, the controller may detect that the patient is awake by detection of ventilation levels, respiratory rates or breathing patterns representative of a waking state or by a level detector which detects that the patient is sitting up.

Alternatively, the blower control may respond to signals or derived indices indicative of sleep by switching off the 'easy speak' mode. For example, rapid eye movement ("REM") is a readily detectable indication of a certain phase of sleep, and slow-wave sleep may also be detected.

Alternatively, the easy speak mode may remain in standby mode for the entire duration of the treatment session and activate whenever sleep is detected by the patient. Some patients may naturally talk during sleep, and the easy speak mode may still serve to reduce patient arousal or disturbance by reducing the air flow out of the mouth during such sleep-talking.

In one embodiment, the apparatus includes a microphone to pick up the voice of a patient. This microphone may be incorporated into the flow generator (with its electrical interface) or may be independent from the flow generator and have a cable to connect to the flow generator. This would allow the microphone to be situated on the flow generator, mask, tube, or even bedding or bed. Preferably, the microphone is in the air channel and part of the tube or independent connector so that it does not need replacing with different masks or other components.

Figure 3A:
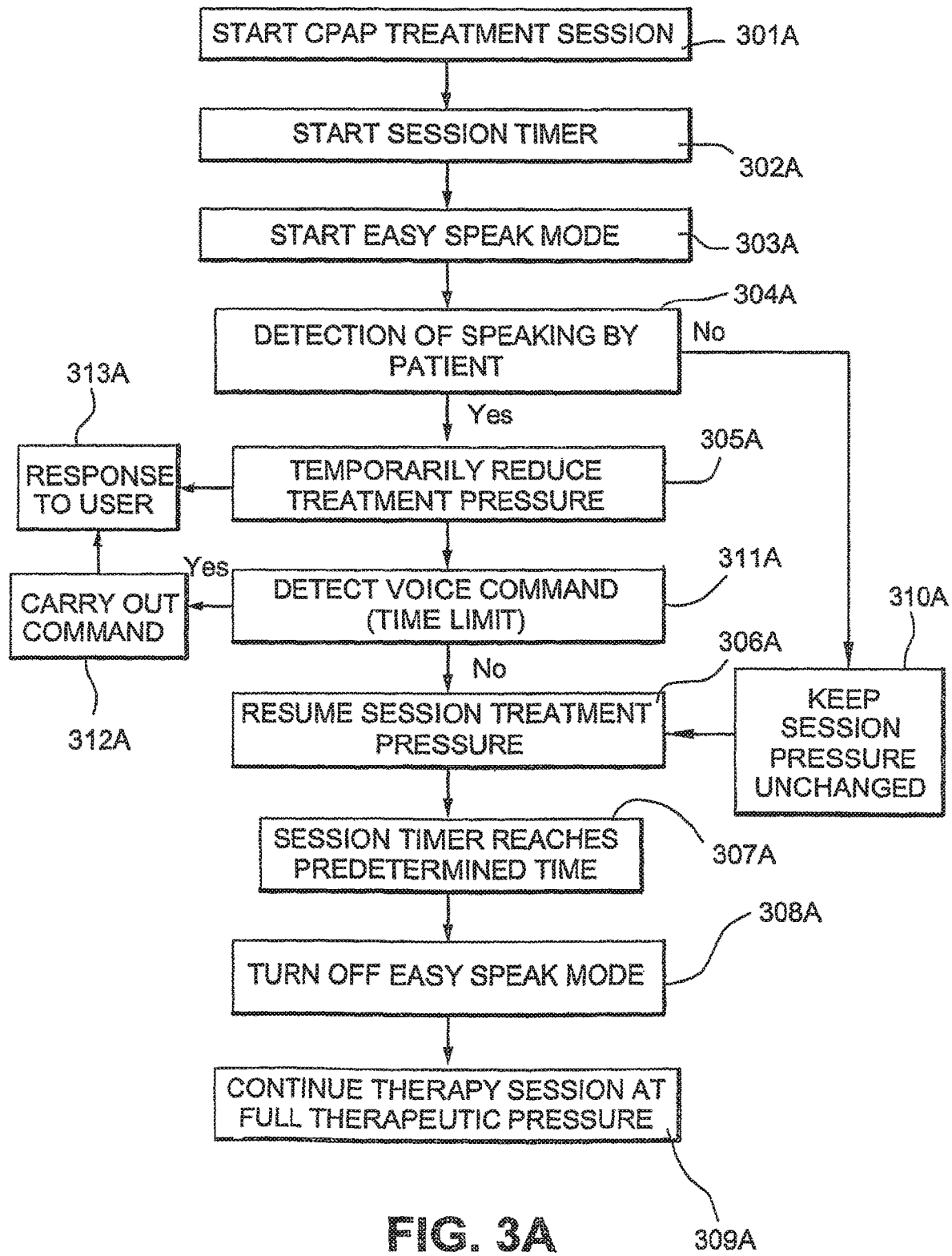
FIG. 3A is a flowchart of a modification of the method of FIG. 3, including detection and execution of voice activated commands according to an embodiment of the invention.

FIG. 3A illustrates a modification of the method of FIG. 3, including voice activation of commands.

Steps 301A-310A are similar to steps 301-310 of FIG. 3 described above. Upon reducing the treatment pressure (at step 305A), the machine is programmed to detect recognized voice commands from the user occurring within a predetermined time (step 311A), for example 2 to 60 seconds. If no such command is detected, the treatment pressure is resumed (at step 306A) as per FIG. 3. If however a recognized voice command is detected within the preset time, the processor will carry out the command (step 312A), optionally provide a response to the user (step 313A)—such as an audible, tactile or visual response—and continue voice command detection for the predetermined time. If no further voice commands are detected, the treatment pressure will be resumed (at step 306A).

In order to detect talking and lower the pressure ready for speech or voice commands, an in-line pressure sensor at the flow generator could be used.

This may be similar to the snore sensor used for the current ResMed S8 Autoset machine. The sensor may be any type of microphone sensor but in one embodiment may be a pressure or flow sensor such as a piezo-resistive or capacitive pressure sensor mounted at the flow generator outlet as per our snore sensor. A fast response time is preferred, for example around 1 ms response, the signal may be amplified and filtered. Preferably, a frequency bandwidth which incorporates that of higher frequency speech is used, however for the control of pressure to allow speech and possibly simple commands a bandwidth of 30-200 Hz such as that in the Autoset snore signal may be sufficient.

In order to assist the differentiation between snore and speech, the likelihood that speech will be on the expiration component of the cycle can be used, also snore is more likely (but not always) to be on inspiration. Thus, detection of speech may be limited to the expiration part of the respiratory cycle.

In any event, as previously stated, the Easy speak feature is preferably disabled after the ramp period, and during the ramp period it is unlikely that the patient will snore. Also, the Easy speak option is preferably switched on only after the 'smartstart' feature (U.S. Pat. No. 6,240,921) is switched off.

Other identifying features of speech which may be used to distinguish speech from snore are the waveform, amplitude and non-repetitive nature of speech.

As speech generally occurs on expiration, a further mitigating feature that could be used is the lowering of EPR (expiration pressure) only when speech is detected, and employing continued inspiratory pressure support with a fast pressure rise time. Thus, in the event of a false positive detection of speech, treatment is not withdrawn on inspiration.

Especially when a nasal mask is used, the component phonemes of the patient's speech are altered by the mouth leak caused by application of the treatment pressure, and the voice recognition system preferably has capability to compensate for this. For example, the recognition may give emphasis to those characteristics of speech which are less affected by the treatment pressure (such as stress, rhythm and pitch) or to process the sound to identify and restore the lost speech elements. Alternatively, or in addition, the voice recognition may be programmed to recognise alternative forms of the commands both with and without the application of the treatment pressure.

With a nasal mask, in order to activate the Easy speak function, humming may be used to produce a pressure signal at the flow generator if this is to be used rather than a mask or tube mounted pressure signal or microphone, in order to ensure sufficient signal when flow is exiting the mouth. In any event, humming may be a good way to trigger the treatment pressure to be lowered, prior to talking or voice commands occurring. In this way, the treatment pressure may be reduced prior to talking, and the sometimes unpleasant sensation of talking with a nasal mask on may be avoided.

Where a full face mask is used, the sensation of talking with the mask on is not as unpleasant, and either humming or talking may be used as the trigger for the Easy speak and voice command functions.

In another embodiment, an Easy speak algorithm may detect speech and then drop the pressure, e.g., to 4 cmH$_2$O, for a period of time, e.g., 5 seconds. The 5 second timeout is reset every time speech is detected. Thus, the pressure remains low until 5 seconds after the patient stops talking. This algorithm may be implemented on existing devices, e.g., ResMed's S8 Autoset. For example, the algorithm may be implemented as a pure software solution. Thus, no electrical or mechanical modifications are necessary.

Inputs to the algorithm include the flow generator output flow and the snore signal. The snore signal may be a low pass filtered absolute value of the high pass filtered pressure, similar to the "rms" of the AC pressure signal.

In the algorithm, the derivative of the flow is calculated. There may be a number of filters in the calculation of the snore, which may cause the snore signal to be delayed. Therefore, the flow derivative may be also delayed in order to facilitate timing of the threshold comparisons. For example, the delay in an implementation may be 31 samples which corresponds to 310 ms.

In an embodiment, Easy speak may be triggered by two methods. The first may be patient humming which causes a relatively large snore signal. The second may be the assumption that when using a nasal mask, when you open your mouth to speak, a sudden rush of air is released from the mouth. This corresponds to a large positive flow derivative.

The algorithm checks these signals against empirically determined thresholds and Easy speak is activated when these signals are above the thresholds. So, if the snore signal is relatively loud (e.g., due to humming) or the flow derivative and snore signal are high, Easy speak is triggered.

For example:

```
If (snore > SNORE_THRESHOLD_HUMMING) then
    Easy speak triggered
Else if( (snore > SNORE_THRESHOLD) AND (flow_derivative > FLOW_DERIVE_THRESHOLD) then
    Easy speak triggered
End
```

Exemplary empirically derived constants are shown in the below chart. The chart shows the magnitude of the difference between the thresholds.

| Constant | Value | Used in |
|---|---|---|
| SNORE_THRESHOLD_HUMMING | 1000 | "Humming" detection |
| SNORE_THRESHOLD | 100 | Open mouth speech |
| FLOW_DERIVE_THRESHOLD | 20 | Open mouth speech |

The combination of the flow derivative and snore signal may be used because flow noise by breathing/leak is of similar magnitude to the normal speech signal. This may need to be modified for a full-face mask as there is not the sudden rush of air from the mouth when speaking.

Mask Leak Control

In a further embodiment of the invention, described with reference to FIGS. 4 and 5, the response of the blower to changes indicative of excessive air leakage at the patient interface is controlled for improved patient comfort and compliance and reduced possibility of disturbance.

Figure 4:
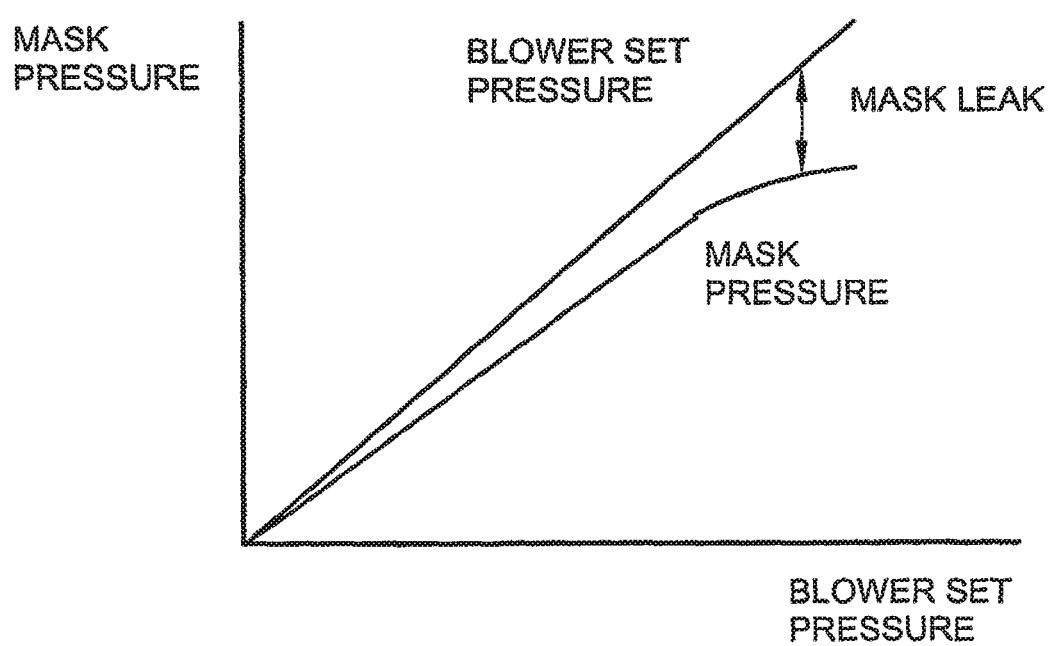
FIG. 4 is a graph of a mask pressure against blower set pressure, showing mask leak.

FIG. 4 is a schematic graph of mask pressure against flow generator pressure illustrating mask leak where the mask is not sitting properly and sealing completely on the patient's face, for example where the mask and headgear has not been optimally adjusted or where the patient may have partially dislodged the mask during sleep.

With reference to FIG. 4, the blower set pressure is on the x axis and the mask pressure on they axis.

It can seen that the pressure lost due to mask leak is the vertical distance between the mask pressure curve and the 45° line. In a typical situation, the mask leak at lower blower pressures will be approximately linear with blower pressure, but above a certain blower pressure will begin to depart more significantly from the blower pressure as the increased pressure causes a significant increase in mask leakage. The point at which this departure commences, and the gradient of this departure, will depend on the type and fit of the mask to the patient, and may also vary from one session to the next, or within a therapy session, depending on the patient's sleeping position.

In prior art APAP machines, air leakage at the mask is detected by a drop in the mask pressure, and the response of the blower as governed by the controller is to increase the blower pressure to compensate. However, in some instances this increased pressure merely serves to further reduce the sealing of the mask onto the patient's face, and the increased pressure is wholly or largely lost by increased leakage. In such instances, the volume of air being leaked is increased with little or no net benefit to efficacy of the therapy, and with increased chance of arousal of or disturbance to the patient and/or the bed partner.

In the present embodiment of the invention, the response of the blower to detection of mask leak is modified.

Figure 5:
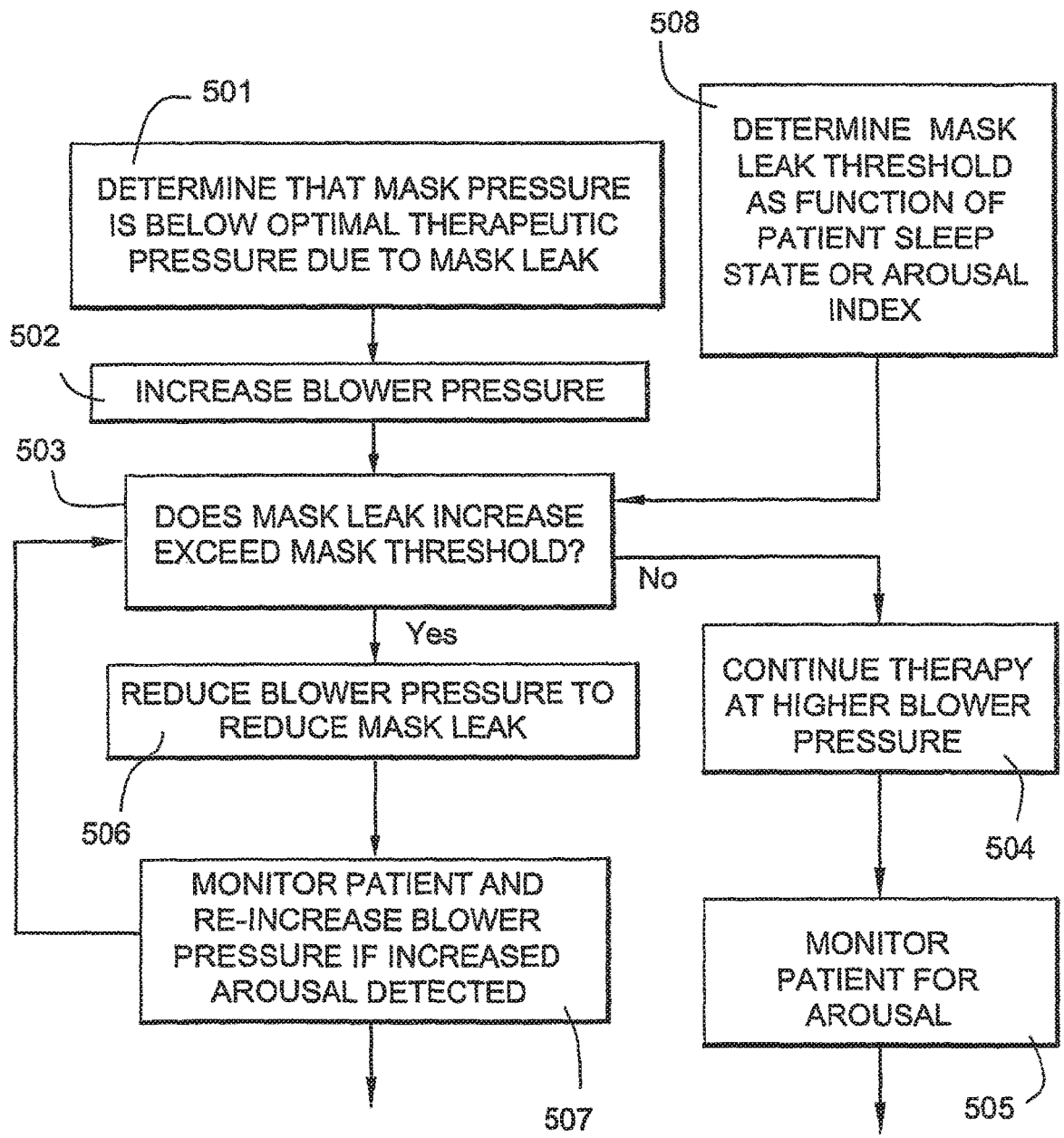
FIG. 5 is a flowchart illustrating mask leak control according to an embodiment of the invention.

FIG. 5 is a flowchart illustrating the steps of the mask leak control method according to an embodiment of the invention.

At first detection of excessive mask leak (step 501), for example as determined by low mask pressure, by an excessive differential between the blower pressure and the pressure at the mask or by a computed mask impedance parameter below a certain threshold, the blower controller causes an increase in the blower pressure (step 502) to compensate for the leak and maintain the therapeutic pressure to desired levels, thus moving further to the right along the mask pressure curve of FIG. 4.

Another determination of mask pressure is made (step 503) and, if the increased blower pressure has corrected the mask pressure to compensate for the leakage then the higher blower pressure is continued (step 504). The patient continues to be monitored for arousal (step 505).

If however the increased blower pressure has resulted in less than a predetermined pressure increase in the mask, or a greater than predetermined flow volume increase, this means that the blower is operating at a low-gradient part of the mask pressure curve of FIG. 4. In this case, the controller is programmed to then recognize that the pressure increase has wholly, or mostly, been ineffectual due to increased leakage at the mask.

When detecting this condition, the controller is programmed to then reduce the blower pressure (step 506) (for example, by a set percentage of the treatment pressure or to the ramp start pressure) or to inhibit further increases in the flow generator output pressure.

The mask leak threshold against which the increased mask leak is compared (step 508) may be a fixed quantity or proportion, for example where a 2 $cmH_2O$ increase in blower results in less than a 1 $cmH_2O$ pressure increase at the mask.

Alternatively, the mask leak threshold may vary as a function of a patient sleep phase indicator so that a greater amount of mask leakage is tolerated if the patient is in a heavier phase of sleep and thus less likely to be disturbed, or if other indicators of disturbance of the patient—such as respiratory rate—remain low. Indicators of sleep phase are known per se in sleep medicine and include monitoring of brain waves and/or respiration.

In a further alternative form of this embodiment, the mask leak threshold may vary as a function of indications of flow limitation, such as flow flattening, snore, apnea and hypopnea, or the Apnea Hypopnea Index (AHI), so that a greater amount of mask leakage is tolerated if the patient is more in need of higher treatment pressure. The blower controller is preferably programmable by the clinician to adjust the mask leak threshold, or turn off the mask leak control function, for patients with historically high flow limitation measurements.

By reducing or capping the blower set pressure in circumstances of high mask leakage, rather than increasing the pressure further as was done in the prior art, disturbance of the patient and/or bed partner by the noise or air flow caused by excessive air leakage is minimized. While the therapy may continue at sub-optimal pressure, it may continue to provide some airway support and is considered that this may in many instances be preferable to waking the patient or having the patient remove the mask during sleep. The former is a substantial patient comfort and compliance issue and the latter may deny the patient the entire benefit of the therapy.

Furthermore, by reducing the blower set pressure in response to excessive mask leak, the mask may settle back into improved conformity with the patient's face and the mask leakage be reduced, thus altering the mask pressure curve shown in FIG. 4 to one closer to the 45° line.

The controller may be programmed to make one or more further attempts to ramp up blower pressure after a predetermined time periods, for example 15 minutes, have elapsed to reassess the quality of the mask-to-patient seal.

The controller may also be programmed to monitor in real time the patient's AHI and other patient arousal and flow limitation indicators, to detect any reduction in effectiveness of therapy at the lower pressure. If the indicators show increased flow limitation and/or patient arousal at the lower treatment pressure, indicative of insufficient treatment pressure for airway stability, the controller will re-increase the blower pressure (step 507).

Patient arousal may also be sensed by monitoring body positions. Continual movement, if detected in conjunction with high leak, may indicate patient arousal due to mask leak.

Snoring is indicative of airway narrowing, and may be used as an indicator that the treatment pressure is too low and must be increased regardless of leak.

In essence, this embodiment seeks to apply the lowest pressure required to treat the patient effectively and limits maximum pressure in circumstances of mask leak, whereas previous treatments did only the former. In this way, a balance is achieved between patient arousal due to mask leak and effectiveness of the treatment, to help maintain patient compliance with the therapy.

The controller keeps a record of incidents where the blower pressure is reduced in response to excessive mask leak, for subsequent review by the clinician to help with mask selection and adjustment for the patient.

Also, at the end of a session where excessive mask leak has been detected, the controller may cause to be displayed on the machine a message alerting the patient to the need to adjust the fit of the mask, and/or to contact the clinician.

The CPAP machine may have two leak control modes, and controls for selecting between these modes depending for example on patient preference and compliance levels. In a first of these modes, which for example may be selected for less compliant patients, the machine on detection of a leak reduces the treatment flow/pressure and maintains the pressure at a below full-therapeutic to allow the mask to seal against the patient's face.

In the second mode of the leak control method, the flow/pressure is reduced to a sub-therapeutic pressure for a brief predetermined period, for example 15-60 seconds, to allow the mask to reseal against the patient's face, and then is ramped back up to therapeutic pressure.

In a further embodiment, a mask seal testing and mask fitting regimen is provided wherein the mask is fitted to the patient in a clinical setting and the device switched to a "mask fitting" operational mode. In this mode, the flow generator is controlled to apply a normal range treatment pressure, with the flow rate limited to a flow approximately equal to or slightly above the vent flow rate for the mask.

If the mask seals well, the pressure at the mask will be at or near full therapeutic pressure. If there is a substantial mask leak, this may be detected by insufficient pressure in the mask, without the noisy operation and large volume air leaks which the prior art low pressure-high volume mask fitting modes regimens. In this way, the mask fit may be adjusted without undue noise and a large volume of air flow rushing past the patient's face, and a further hurdle to patient adoption of and compliance with the therapy is reduced.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A continuous positive airway pressure system (CPAP) comprising:
   a flow generator configured to provide a continuous flow of breathable gas at a positive airway pressure to at least one upper airway of a patient;
   a patient interface structured to engage with the at least one upper airway of the patient to deliver the continuous flow of breathable gas at the positive airway pressure, the continuous flow of breathable gas at the positive airway pressure to splint open the at least one upper airway;
   a microphone configured to detect audio in vicinity of the patient; and
   at least one hardware processor that is coupled to the microphone, the at least one hardware processor configured to:
      determine at least one physical quantity related to the patient while the patient interface is engaged with the at least one upper airway of the patient and the breathable gas is being provided thereto;
      determine, using the determined at least one physical quantity, a sleep state of the patient;
      based on the determined sleep state of the patient, activate or deactivate a voice-command mode for the CPAP system, wherein the voice command mode is for recognizing voice commands;
      during a time period in which the voice-command mode of the CPAP system is activated:
         receive signals that are indicative of speech from the patient,
         recognize patient speech based on the received signals, and
         trigger functionality of the CPAP system based on the recognized patient speech; and
      deactivate the voice-command mode for the CPAP system based on determination that the sleep state indicates the patient is sleeping, wherein voice commands are not used to trigger functionality of the CPAP system when the voice-command mode is deactivated,
   wherein the continuous flow of breathable gas at the positive airway pressure to the at least one upper airway of the patient is provided while the voice-command mode is deactivated.

2. The CPAP system of claim 1, wherein the at least one physical quantity is detection of ventilation levels, respiratory rates, breathing patterns, rapid eye movement (REM) sleep, slow-wave sleep, and/or posture of the patient.

3. The CPAP system of claim 1, further comprising:
   at least one sensor configured to detect at least one attribute of the patient that is related to an attempt by the patient to speak,
   wherein the at least one hardware processor is further configured to:
      determine, during application of the continuous positive airway pressure and based on the detected at least one attribute, when the patient is attempting to speak; and
      responsive to determination that the patient is attempting to speak, automatically reduce a pressure of the continuous flow of breathable gas while the flow generator continues to provide the continuous flow of breathable gas.

4. The CPAP system of claim 3, wherein pressure supplied during the expiration phase of the respiratory cycle of the patient is changed more than the pressure supplied during inspiration of the respiratory cycle of the patient.

5. The CPAP system of claim 3, wherein the received signals that are recognized as indicative of speech are recognized as such while the pressure of the continuous flow of breathable gas is reduced.

6. The CPAP system of claim 3, wherein the at least one sensor is a pressure sensor, second microphone sensor, flow sensor, or a snore sensor.

7. The CPAP system of claim 3, wherein the at least one hardware processor is further configured to:

upon determination that no speech has been determined for at least a predetermined period of time, control the flow generator to increase the pressure of the continuous flow of breathable gas.

8. The CPAP system of claim 7, wherein the pressure is increased to a level that is similar to a pressure level provided prior to the automatic reduction in pressure.

9. The CPAP system of claim 7, wherein determination of the patient attempting to speak includes determination of a snore signal above a snore threshold and/or determination of a positive flow derivative above a flow threshold.

10. The CPAP system of claim 1, wherein the sleep state includes an awake state of the patient or a sleeping state of the patient.

11. The CPAP system of claim 10, wherein the sleeping state is a rapid eye movement (REM) state or a slow-wave sleep state.

12. The CPAP system of claim 1, wherein the functionality of the CPAP system that is triggered causes airflow out of the mouth of the patient to be reduced.

13. A continuous positive airway pressure system (CPAP) comprising:
   a flow generator configured to provide a continuous flow of breathable gas at a positive airway pressure to at least one upper airway of a patient;
   a patient interface structured to engage with the at least one upper airway of the patient to deliver the continuous flow of breathable gas at the positive airway pressure, the continuous flow of breathable gas at the positive airway pressure to splint open the at least one upper airway;
   a microphone configured to detect audio in vicinity of the patient; and
   at least one hardware processor that is coupled to the microphone, the at least one hardware processor configured to:
      determine at least one physical quantity related to the patient while the patient interface is engaged with the at least one upper airway of the patient and the breathable gas is being provided thereto;
      determine, using the determined at least one physical quantity, a sleep state of the patient;
      based on the determined sleep state of the patient, activate or deactivate a voice-command mode for the CPAP system, wherein the voice command mode is for recognizing voice commands;
      during a time period in which the voice-command mode of the CPAP system is activated:
         receive signals that are indicative of speech from the patient,
         recognize patient speech based on the received signals, and
         trigger functionality of the CPAP system based on the recognized patient speech; and
      deactivate the voice-command mode for the CPAP system based on determination that the sleep state indicates the patient is sleeping, wherein voice commands are not used to trigger functionality of the CPAP system when the voice-command mode is deactivated,
      wherein signals that are received during inspiration by the patient are ignored while signals received during expiration are used for recognizing voice commands.

14. A continuous positive airway pressure system (CPAP) comprising:
   a flow generator configured to provide a continuous flow of breathable gas at a positive airway pressure to at least one upper airway of a patient;
   a patient interface structured to engage with the at least one upper airway of the patient to deliver the continuous flow of breathable gas at the positive airway pressure, the continuous flow of breathable gas at the positive airway pressure to splint open the at least one upper airway;
   a microphone configured to detect audio in vicinity of the patient; and
   at least one hardware processor that is coupled to the microphone the at least one hardware processor configured to:
      determine at least one physical quantity related to the patient while the patient interface is engaged with the at least one upper airway of the patient and the breathable gas is being provided thereto;
      determine, using the determined at least one physical quantity, a sleep state of the patient;
      based on the determined sleep state of the patient, activate or deactivate a voice-command mode for the CPAP system, wherein the voice command mode is for recognizing voice commands;
      during a time period in which the voice-command mode of the CPAP system is activated:
         receive signals that are indicative of speech from the patient,
         recognize patient speech based on the received signals,
         trigger functionality of the CPAP system based on the recognized patient speech, and
         cause an audible, tactile, or visual response that indicates recognition of the patient speech and/or activation of triggering of the functionality of the CPAP system based on the recognized patient speech; and
      deactivate the voice-command mode for the CPAP system based on determination that the sleep state indicates the patient is sleeping, wherein voice commands are not used to trigger functionality of the CPAP system when the voice-command mode is deactivated.

15. A method of operating a continuous positive air pressure (CPAP) system, the method comprising;
   providing, via a flow generator that includes an impeller, a continuous flow of breathable gas at a positive airway pressure to a patient interface structured to engage with the at least one upper airway of the patient to deliver the continuous flow of breathable gas at the positive airway pressure to splint open the at least one upper airway;
   determining, using a controller that includes at least one processor, at least one physical quantity related to the patient while the patient interface is engaged with the at least one upper airway of the patient and the breathable gas is being provided thereto;
   determining, using the determined at least one physical quantity, a sleep state of the patient;
   based on the determination of the sleep state of the patient, activating or deactivating a voice-command mode for the CPAP system, wherein the voice command mode is for recognizing voice commands;
   during a time period in which the voice-command mode of the CPAP system is activated:
   receiving, via a microphone that is part of the CPAP system, signals that are indicative of speech from the patient,
      recognizing patient speech based on the received signals, and triggering functionality of the CPAP system based on the recognized patient speech; and deactivating the voice-command mode for the CPAP system based on determination that the sleep state indicates the patient is sleeping, wherein functionality of the CPAP system is not triggered from patient speech when the voice-command mode is deactivated, wherein the continuous flow of breathable gas at the positive airway pressure to the at least one upper airway of the patient is provided while the voice-command mode is deactivated.

16. The method of claim 15, further comprising:

detecting at least one attribute of the patient that is related to an attempt by the patient to speak;

determining, during application of the continuous positive airway pressure and based on the detected at least one attribute, when the patient is attempting to speak; and responsive to determination that the patient is attempting to speak, automatically reducing a pressure of the continuous flow of breathable gas while the flow generator continues to provide the continuous flow of breathable gas.

* * * * *